United States Patent [19]

Shibasaki et al.

[11] Patent Number: 5,053,526
[45] Date of Patent: Oct. 1, 1991

[54] PHARMACEUTICALS CONTAINING PROSTAGLANDIN $I_2$

[75] Inventors: Masakatsu Shibasaki, Tokyo; Mikiko Sodeoka; Yuji Ogawa, both of Sagamihara; Toshiaki Mase, Sagamihara; Akira Ishibashi, Ami; Daijiro Horii, Sakura; Toshiji Kanayama, Ami; Katsuhiko Iseki, Abiko; Masaki Shinoda; Chiyoko Ishiyama, both of Ami; Yoshio Hayashi, Ushiku, all of Japan

[73] Assignees: Mitsubishi Kasei Corporation; Sagami Chemical Research Center, both of Tokyo, Japan

[21] Appl. No.: 511,945

[22] Filed: Apr. 16, 1990

Related U.S. Application Data

[63] Continuation of Ser. No. 333,733, Apr. 3, 1989, abandoned, which is a continuation of Ser. No. 206,943, Jun. 13, 1988, abandoned, which is a continuation of Ser. No. 99,779, Sep. 22, 1987, abandoned, which is a continuation of Ser. No. 763,618, Aug. 8, 1985, Pat. No. 4,699,921.

[30] Foreign Application Priority Data

Aug. 9, 1984 [JP] Japan .................... 59-165669
Jul. 31, 1985 [JP] Japan .................... 60-167681

[51] Int. Cl.$^5$ .................................. C07L 177/00
[52] U.S. Cl. .................................. 560/119; 562/501
[58] Field of Search .................. 560/119; 562/501

[56] References Cited

U.S. PATENT DOCUMENTS 4,699,921 10/1987 Shibasaki .................. 560/121
4,774,341 9/1988 Shibasuki .................. 549/214
4,777,184 10/1988 Kojima .................. 514/530

FOREIGN PATENT DOCUMENTS 134153 3/1985 Japan .................. 560/119

Primary Examiner—Robert Gerstl
Attorney, Agent, or Firm—Foley & Lardner

[57] ABSTRACT

Disclosed is a pharmaceutical having circulation ameliorating effect and antiulcer effect containing a prostaglandin $I_2$ analogue represented by the formula shown below or a non-toxic salt of its salt or a cyclodextrin inclusion compound thereof as the effective ingredient:

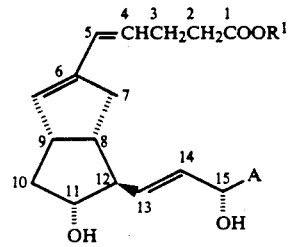

wherein $R^1$ represents a hydrogen atom, an alkyl group having 1 to 12 carbon atoms, a cycloalkyl group having 4 to 7 carbon atoms or a phenyl group; A represents a pentyl group, a cyclopentyl group, a cyclohexyl group, a 1-methyl-3-hexynyl group, a 2-methyl-3-hexynyl group, a 1-methylhexyl group, a 2-phenethyl group, a 1,1-dimethylpentyl group, a 2-methylpentyl group, a 1-cyclohexylethyl group, a 2-methylhexyl group, a 1-methyl-3-pentynyl group or 1 2,6-dimethyl-5-heptenyl group; the double bond between the carbon atoms at 4- and 5-positions is E or Z or a mixture thereof, the asymmetric center in the substituent represented by A is R-configuration or S-configuration or a mixture thereof.

The pharmaceuticals containing, as an active ingredient, prostaglandin $I_2$ analogues of the present invention have potent platelet aggregation inhibiting effect, blood pressure depressing effect, vasodilative effect and antiulcer effect, and are also low in toxicity.

4 Claims, No Drawings

PHARMACEUTICALS CONTAINING PROSTAGLANDIN I₂

This application is a continuation of application Ser. No. 07/333,733, filed April 3, 1989, now abandoned which is a continuation of application Ser. No. 07/206,943 filed June 13, 1988 now abandoned, which is a continuation of application Ser. No. 07/099,779 filed Sept. 22, 1987 now abandoned which is a continuation of application Ser. No. 06/763,618 filed Aug. 8, 1985 now U.S. Pat. No. 4,699,921 issued Oct. 13, 1987.

BACKGROUND OF THE INVENTION

This invention relates to prostaglandin I₂ analogues and uses thereof for circulation ameliorating pharmaceuticals for blood flow amelioration, antithrombotic or antiulcer pharmaceuticals.

Prostaglandin I₂ (hereinafter written as PGI₂) has been known as a natural physiologically active substance and has the stucture shown by the following formula:

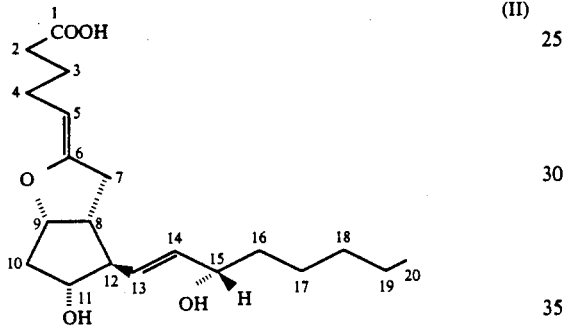

Its chemical name is (5Z,13E)-(9α,11α,15S)-6,9-epoxy-11, 15-dihydroxyprost-5,13-dienic acid. PGI₂ exists within the vascular walls and is the most potent inhibitor of platelet aggregation as well as being a powerful vasodilator [Nature, 263, 663 (1976)].

PGI₂ exhibiting such properties is useful for prophylaxis and therapy of cerebral thrombosis, myocardial infarction and acute stenocardia induced by exasperation of platelet aggregation and further increase of thrombotic tendency, expected to be appicable for prophylaxis and therapy of arteriosclerotic diseases and desired to be developed as the so-called circulation ameliorating or antithrombotic pharmaceuticals.

Also, many prostaglandins containing PGI₂ are known to have gastric mucosa protective effect and blood flow increasing effect within gastric mucosa ['83 Inflammation Seminar "Prostaglandin" Pretext page 50 (sponsored by Society of Inflammation of Japan)], and PGI₂ having such effects can be expected to be applicable for prophylaxis and therapy of gastrointestinal ulcers, typically stomach ulcer.

However, PGI₂ is remarkably unstable and this has been an obstacle against practical application as pharmaceuticals.

In order to overcome such an obstacle, studies have been made about stable analogues in which the oxygen atom between the carbon atoms at the 6- and 9-positions in PGI₂ is replaced with carbon atom. The carbacycline type compounds [Japanese Provisional Patent Publication No. 130543/1979] of the chemical formula (III) as represented by OP-41483 [Japanese Provisional Patent Publication No. 130543/1979] ? $^{-1}$ 9(0)-methano-Δ⁶- PGI₁ of the chemical formula (IV) [Japanese Provisional Patent Publication No. 32426/1981] are all chemically stable PGI₂ analogues. Also, 9(0)-methano-Δ⁶⁽⁹ᵅ⁾-prostaglandin I₁ (isocarbacyclin [Tetrahedron Letters, 24, 3493 (1983)], chemical formula (V)) in which the 5-position double bond in 9(0)-methano-prostacyclin (carbacyclin) is transferred to the 6(9α) position is also chemically sufficiently stable and has been reported as a PGI₂ analogue having potent physiological properties [Japanese Provisional Patent Publication No. 137445/1984].

[OP-41483 A = cyclooentyl]

SUMMARY THE INVENTION

The present inventors have made extensive studies in order to provide prostaglandin I₂ analogues which are stable, substantially free from decomposition at room temperature and have excellent pharmacological properties, and consequently created novel prostaglandin I₂ analogues and found that said analogues have potent platelet aggregation inhibiting effect, hypotensive effect, vasodilative effect and antiulcer effect, and are also low in toxicity, to accomplish the present invention.

Thus, the present invention provides a pharmaceutical containing a prostaglandin I₂ analogue represented by the formula (I):

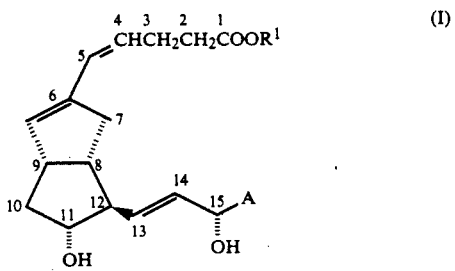

wherein R¹ represents a hydrogen atom, an alkyl group having 1 to 12 carbon atoms, a cycloalkyl group having 4 to 7 carbon atoms or a phenyl group, A represents a pentyl group, a cyclopentyl group, a cyclohexyl group, a 1-methyl-3-hexynyl group, a 2-methyl-3-hexynyl group, a 1-methylhexyl group, a 2-phenethyl group, a 1,1-dimethylpentyl group, a 2-methylpentyl group, a 1-cyclohexylethyl group, a 2-methylhexyl group, a 1-methyl-3-pentynyl group or a 2,6-dimethyl-5-heptenyl group, the double bond between the carbon atoms at 4- and 5-positions is E or Z or a mixture thereof, the asymmetric center in the substituent represented by A is R-configuration or S-configuration or a mixture thereof,
as the effective ingredient.

PREFERRED EMBODIMENTS OF THE INVENTION

The compound of the present invention was found to exhibit potent platelet aggregation inhibiting effect, vasodilatory effect, hypotensive effect and antiulcer effect in animal experiments. Such platelet aggregation inhibiting effect and vasodilatory effect suggest that the present compound is an excellent blood flow ameliorating agent or an antithrombotic drug for prophylaxis or therapy against cerebral thrombosis, myocardial infarction, acute stenocardia, peripheral circulation disorders, etc. caused by platelet aggregation exasperation or arteriosclerosis. Further, the hypotensive effect suggests that the present compound is an excellent antihypertensive for prophylaxis or therapy against hypertensions. Moreover, the antiulcer effect suggests that the present compound is an excellent antiulcer drug for prophylaxis or therapy against gastrointestinal ulcers, typically stomach ulcer.

In the animal experiments, the compound of the present invention proved to be low in toxicity, and this fact suggests that it is an excellent pharmaceutical with high safety.

In the compounds of the present invention represented by the above formula [I], $R^1$ represents a hydrogen atom, an alkyl group having 1 to 12 carbon atoms, a cycloalkyl group having 4 to 7 carbon atoms or a phenyl group. The alkyl group having 1 to 12 carbon atoms may include straight or branched alkyl groups such as methyl, ethyl, n-propyl, iso-propyl, n-butyl, sec-butyl, tert-butyl, n-pentyl, iso-amyl, n-hexyl, n-heptyl, n-octyl, n-nonyl, n-decyl, n-undecyl, n-dodecyl and the like. The cycloalkyl group having 4 to 7 carbon atoms may be exemplified by cyclobutyl, 1-propylcyclobutyl, cyclopentyl, 2-pentylcyclopentyl, cyclohexyl, 3-ethylcyclohexyl, cycloheptyl and the like.

Specific examples of the prostaglandin $I_2$ analogues provided by the present invention may include 3-(4'carboxy-1'-butenyl) -6(S)-(3'(S)-hydroxy-trans-1'-octenyl)-7(R)-hydroxy-(1S,5S)-cis-bicyclo [3.3.0]oct-2-ene (Compound A) and its methyl ester (Compound A'), 3-(4'-carboxy-1'-butenyl) -6(S)-(3'(S)-hydroxy-3'-cyclopentyltrans-1'-propenyl) -7(R)-hydroxy-(1S,5S)-cis-bicyclo[3.3.0]oct-2-ene (Compound B) and its methyl ester (Compound B'), 3-(4'-carboxy-1'-butenyl)-6(S)-(3'(S)-hydroxy-4'(RS) -methyl-trans-1'-octen-6'-ynyl)-7(R)-hydroxy-(1S,5S)-cis-bicyclo[3.3.0]oct-2-ene (Compound C) and its methyl ester (Compound C'), 3-(4'-carboxy-1'- butenyl)-6(S)-(3'(S)-hydroxy-5'(R)-methyl-9'methyl-trans-1'-decen-8'-enyl)-7(R)-hydroxy-(1S, 5S)-cis-bicyclo[3.3.0]oct-2-ene (Compound D) and its methyl ester (Compound D'), 3-(4'-carboxy-1'-butenyl)-6(S)-(3'(S)-hydroxy-3'-cyclohexyl-trans -1'-propenyl)-7(R)-hydroxy(1S,5S) -cis-bicyclo[3.3.0]oct-2-ene (Compound E) and its ethyl ester (Compound E'), 3-(4'-carboxy-1'-butenyl)6(S)-(3'(S)-hydroxy-4'(RS)-methyl-trans-1'-nonen-6'-ynyl)-7(R)-hydroxy-(1S,5S)-cis-bicyclo [3.3.0]oct-2-ene (Compound F) and its ethyl ester (Compound F'), 3-(4'-carboxy-1'-butenyl) -6(S)-(3'(S)-hydroxy-5'(RS)-methyltrans-1'-nonen-6'-ynyl) -7(R)-hydroxy-(1S,5S)-cis-bicyclo[3.3.0]oct-2-ene (Compound G) and its ethyl ester (Compound G'), 3-(4'-carboxy-1'-butenyl)-6(S)-(3'(S)-hydroxy-4'(RS)-methyl-trans-1'-nonenyl)-7(R)-hydroxy(1S,5S)-cis-bicyclo [3.3.0]oct-2-ene (Compound H) and its ethyl ester (Compound H'), 3-(4'-carboxy-1'-butenyl)-6(S) (3'(S)-hydroxy-5'-phenyl-trans-1'-pentenyl)-7(R)-hydroxy-(1S,5S) -cis-bicyclo[3.3.0]oct-2-ene (Compound I) and its ethyl ester (Compound I'), 3-(4'-carboxy-1'-butenyl)-6(S)-(3'(S)-hydroxy-4',4'-dimethyl-trans-1'-octenyl)-7(R)-hydroxy-(1S,5S)-cis-bicyclo[3.3.0]oct-2-ene (Compound J) and its ethyl ester (Compound J'), 3-(4'-carboxy-1'-butenyl) -6(S)-(3'(S)-hydroxy-5'(RS)-methyltrans-1'-octenyl) -7(R)-hydroxy-(1S,5S)-cis-bicyclo[3.3.0]oct-2-ene (Compound K) and its ethyl ester (Compound K'), 3-(4'-butenyl-1'-butenyl)-6(S)-(3'(S)-hydroxy-4'(RS)cyclohexyl-trans-1'-pentenyl) -7(R)-hydroxy-(1S,5S)-cisbicyclo [3.3.0]oct-2-ene (Compound L) and its ethyl ester (Compound L'), 3-(4'-carboxy-1'-butenyl)-6(S)-(3'(S)-hydroxy-5'(RS)-methyl-trans-1'-nonenyl)-7(R)-hydroxy-(1S,5S) -cis-bicyclo[3.3.0]-oct-2-ene (Compound M) and its 5 ethyl ester (Compound M'), and further inclusion compounds of these compounds and cyclodextrin.

In application of the compounds of the present invention for clinical uses as the blood flow ameliorator, antithrombotic, antihypertensive and antiulcer, the effective administration may be either oral or parenteral, and they can be administered at a dose of 0.1 $\mu$g to 100 mg per one administration, desirably at a daily dose of 1 $\mu$g to 1 mg in one or several divided doses. However, the accurate dosage depends on the age, body weight, severity of disease of the patient, the administration route and the number of administrations.

The solid preparations for oral administration may include tablets, pills, powders and granules. In such solid preparations, one or more active substances may be mixed with at least one inert diluent such as half-digestable starch, potato starch, alginic acid, mannitol or sucrose. The preparation may also contain additives other than diluents, for example, lubricants such as magnesium stearate, according to a conventional manner. The liquid preparations for oral administraton may contain parmaceutically acceptable emulsions, solutions, suspensions or elexirs, and may also contain, in addition to inert diluents in general, auxiliary agents such as wetting agents, suspension aids, sweetners, flavors, aromatics or preservatives. As other preparations for oral administration, there may also be included capsules of absorbable materials such as gelatin containing at least one active substance together with or without diluents or excipients.

As the solid preparation for rectal administration, there may be included suppositories comprising one or more active substance and at least one inert base such as cacao butter, macrogol, Witepsol, and which can be treated according to the method known per se. Further, as the preparation for topical application, ointments, etc. may be employed.

The product for parenteral administration contains sterile aqueous or non-aqueous solvents, suspending agents or emulsifiers. Non-aqueous solvents or suspending agents y include propylene glycol, polyethylene glycol, vegetable oils such as olive oil, injectable organic acid esters such as ethyl oleate. Such preparations can also contain auxiliary agents such as preservatives, wetting agents, emulsifiers and dispersants. They can be sterilized by filtration through a bacteria retaining filter, formulation with a sterilizer or by irradiation. It is also possible to prepare sterile solid preparations which are to be dissolved in a sterile solvent for injection immediately before use.

As for acute toxicity of the compounds of the present invention, in intraveneous administration to mouse, each $LD_{50}$ value of the compounds of the present invention was found to be 1000 μg/kg-animal weight or higher, and no change in state was observed at all at levels of administration of 1000 μg/kg-animal weight or lower.

The compounds of the present invention represented by the formula (I) can be produced according to, for example, the route shown below by use of the known compound (VI) as disclosed together with its synthetic method in [Collected Gists of Lectures, the 45th Symposium on the synthetic organic chemistry (sponsored by The Society of Synthetic Organic Chemistry, JAPAN)].

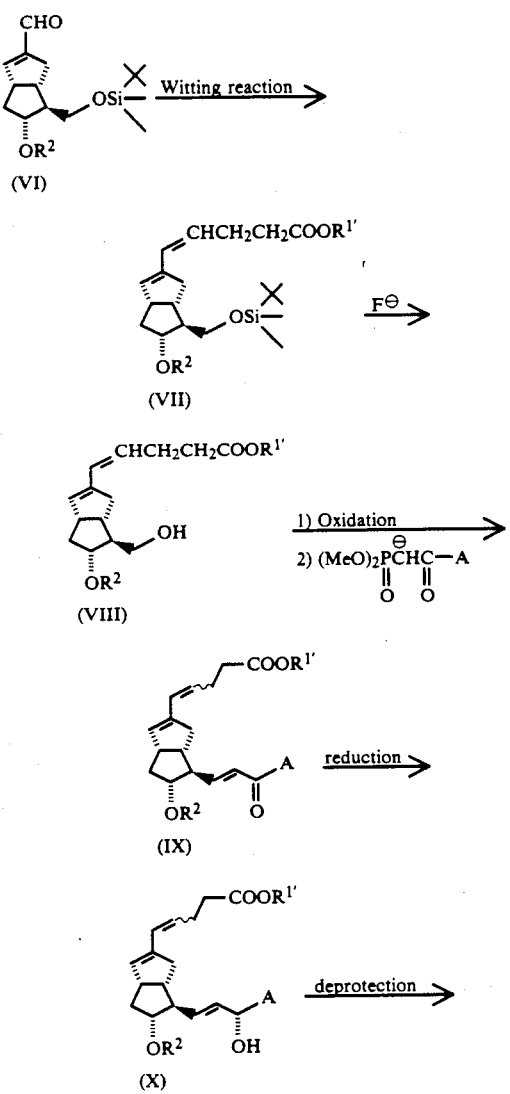

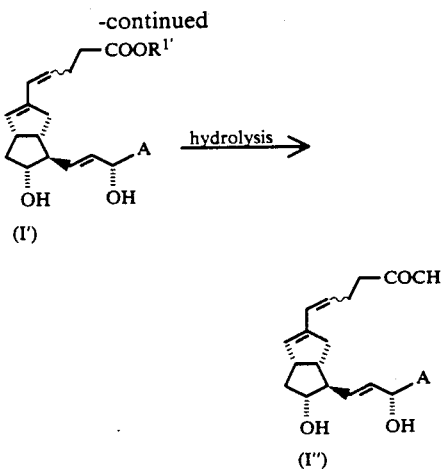

[wherein $R^1$ represents an alkyl group having 1 to 12 carbon atoms, a cycloaklyl group having 4 to 7 carbon atoms or a phenyl group; $R^2$ represents a protective group for a hydroxy group which is eliminable under acidic conditions; and A is the same as defined above].

The compound (VII) can be prepared by allowing the compound (VI) to react with the Wittig reagent obtained by the treatment of $R^3_3P^+CH_2CH_2CH_2CO_2R^{1'}X^-$ [wherein $R^{1'}$ is the same as defined above; $R^3$ is an alkyl group having 1 to 4 carbon atoms or a phenyl group; $X^{31}$ is a halogen atom such as chlorine, bromine, etc.] with a base. As the base, sodium hydride, potassium hydride or potassium tert-butoxide may preferably be employed. The amount of the Wittig reagent may be 1 to 10 equivalents, preferably 1 to 5 equivalents, relative to the starting compound. The reaction solvent may preferably be dimethyl sulfoxide or ethers such as tetrahydrofuran, dimethoxyethane, etc. The reaction temperature may be −78° C. to 50° C., preferably −20° C. to 30° C.

The compound (VIII) can be obtained by treating the compound (VII) with 1 to 10 equivalents, preferably 1 to 3 equivalents of a fluorine compound such as n-butylammonium fluoride or cesium fluoride. The reaction may be carried out in an ether such as tetrahydrofuran, ethyl ether, etc. at a temperature of 0° to 30° C. for about 10 minutes to 3 days.

The compound (IX) can be obtained by oxidizing the hydroxymethyl group in the compound (VIII) to convert it to an aldehyde, and then allowing the aldehyde to react with the Wittig reagent obtained by the treatment of $(R^4O)_2P(O)CH_2C(O)$-A [wherein A is the same as defined above, $R^4$ is an alkyl group having 1 to 3 carbon atoms] with a base. In oxidation of the hydroxymethyl group, it is preferred to employ the oxidation method in which a system of amine/pyridine-sulfur trioxide complex/dimethyl sulfoxide for oxidizing a primary alcohol to aldehyde is employed. The reaction is carried out generally at 10° C. to 40° C. for about 1 minute to 2 hours. The amount of the oxidizing agent used may preferably be in an excess, namely about 2 to 100 equivalents relative to the starting compound (VIII). The aldehyde thus obtained should preferably be subjected as such without purification to the subsequent Wittig reaction. The base to be used in the Wittig reaction should preferably be sodium hydride, potassium hydride or potassium tert-butoxide. The amount of the reagent employed may be 1 to 10 equivalents, preferably 1 to 5 equivalents, relative to the aldehyde. The reaction solvent may preferably be an ether such as tetrahyrofuran, dimethoxyethane, etc., and the reaction may be carried out at a temperature from −20° C. to 50° C. for about 5 minutes to 24 hours. These compounds (VII) to (IX) can be purified according to conventional purification means such as column chromatography, thin layer chromatography, liquid chromatography, etc.

The compound (X) can be obtained by reduction of the compound (IX). As the reducing agent, those which can not reduce COOR$^{1'}$ are preferred. For example, there may be included sodium borohydride, zinc borohydride, diphenyl tin hydride, lithium trialkylborohydride such as lithium tri-sec-butylborohydride, diisobutylaluminum hydride modified with 2,6-di-tert-butyl-4-methylphenol, or lithium aluminumhydride modified with 1,1'-bi-2-naphthol and a lower alcohol such as ethanol and so on. The reaction solvent may include lower alcohols such as methanol, ethanol and the like, ethers such as diethyl ether, tetrahydrofuran and dioxane, or aromatic hydrocarbons such as benzene and toluene. The amount of the reducing agent used may preferably be 0.5 to 30 equivalents, particularly 1 to 10 equivalents, relative to the starting compound, the α,β-unsaturated compound. The reaction temperature may be −150° C. to 80° C., preferably −100° C. to 30° C. The reaction mixture thus obtained may be treated according to the post-treatments as usual. For example, the reaction mixture may be poured into dil. hydrochloric acid, dil. sulfuric acid or an aqueous saturated ammonium chloride solution, extracted with an organic solvent poorly soluble in water such as hexane, pentane, petroleum ether, ethyl ether, benzene or toluene, the combined extracts are washed with an aqueous sodium chloride solution, dried over a drying agent such as anhydrous sodium sulfate, anhydrous magnesium sulfate, anhydrous potassium carbonate, etc., and the organic solvent is evaporated to give a crude product. The crude product can be purified according to purification means such as column chromatography, thin layer chromatography, liquid chromatography, etc., if desired. The product thus obtained may further be subjected to the deprotection reaction, separation of diastereomers, hydrolysis reaction and salt forming reaction, if necessary.

Removal of the protective group on hydroxyl group may be practiced preferably with the use of acetic acid, pyridinium salt of p-toluenesulfonic acid or a cation exchange resin as the catalyst in a solvent such as water, tetrahydrofuran, ethyl ether, dioxane, acetone, acetonitrile, etc. The reaction may be carried out generally at −78° C. to 80° C. for about 10 minutes to 3 days. The product thus obtained may be further subjected to separation of diastereomers based on the 15-position hydroxyl group formed by the reduction reaction by purification according to the purification means such as column chromatography, thin layer chromatography, liquid chromatography, etc.

The hydrolysis reaction of the carboxylic acid ester may be conducted in water, methanol or ethanol alone or a mixture thereof containing caustic soda or caustic potash at a temperature range from −10° C. to 100° C. for one minute to 24 hours, or alternatively by use of an enzyme such as lipase in water or a solution containing water at a temperature range from −10° C. to 60° C. for one minute to 24 hours. The product after hydrolysis can be purified according to the same purification means as mentioned above The present invention is described in more detail by referring to the following Examples.

EXAMPLE 1

Synthesis of Compound A'

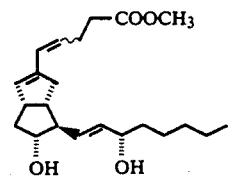

(a) 3-(4'-Methoxycarbonyl-1'-butenyl)-6(S)-(3'-oxo-trans-1'-octenyl)-7(R)-tetrahydropyranyloxy-(1S,5S)-cisbicyclo [3.3.0]oct-2-ene (73 mg, 0.16 mmol) was dissolved in methanol (2.6 ml). To the solution was added sodium borohydride (6 mg, 0.16 mmol) at −25° C. and the mixture was stirred at −25° C. for 40 minutes. After the reaction was stopped with addition of acetone, a saturated aqueous ammonium chloride solution was added thereto. Methanol was distilled out and then the residual aqueous layer was extracted with ether. The extract was washed with a saturated aqueous saline solution and thereafter dried with anhydrous magnesium sulfate. The solvent was distilled out and the residue was purified through silica gel column chromatography to obtain 3-(4'-methoxycarbonyl-1'-butenyl)-6(S)-(3'(RS)-hydroxy-trans-1'-octenyl)7(R)-tetrahydropyranyloxy-(1S,5S)-cis-bicyclo[3.3.0]oct-2-ene (74 mg, Yield: 100%) as a substantially colorless oily product.

IR (neat): 3470, 1745 cm$^{-1}$.

NMR δ(CDCl$_3$): 6.28 (d, J=16Hz, ½H, trans), 6.00 (d, J=11Hz, ⅜H, cis), 5.10–5.75 (m, 4H), 4.67 (1H, m), 3.70 (s, 3H).

Mass m/z: 446, 230.

(b) 3-(4'-Methoxycarbonyl-1'-butenyl)-6(S)-(3'(RS)-hydroxy-trans-1'-octenyl) -7(R)-tetrahydropyranyloxy-(1S,5S) -cis-bicyclo[3.3.0]oct-2-ene (446 mg, 1 mmol) was dissolved in THF (0.26 ml). To the solution was added a 65% aqueous acetic acid solution (2.6 ml) and the mixture was stirred at 50° C. for 2 hours. The reaction mixture was poured into a cooled saturated aqueous sodium hydrogencarbonate solution and extracted with ethyl acetate. The organic layer was washed with a saturated aqueous saline solution and dried with anhydrous magnesium sulfate. The solvent was distilled out and the residue was purified through silica gel column chromatography to obtain 3-(4'-methoxycarbonyl-1'-butenyl)-6(S)-(3'(S)-hydroxy-trans-1'-octenyl)-7(R)-hydroxy-(1S,5S)-cis-bicyclo [3.3.0]oct-2-ene (Compound A') (214 mg, Yield: 59%) as a colorless oily product.

IR (neat): 3400, 1742 cm$^{-1}$.

NMR δ(CDCl$_3$): 6.30 (d, J=15Hz, ½H, trans), 6.02 (d, J=11Hz, ⅜H, cis), 5.00–5.70 (m, 4H), 4.10 (m, 1H), 3.70 (s, 3H), 3.02 (m, 1H).

Mass m/z: 362, 344.

$[α]_D^{20}=-35°$ (c=0.466, MeOH).

EXAMPLE 2

Synthesis of Compound B'

-continued

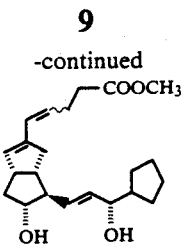

(a) The same reaction procedures were carried out as in Example 1-(a) except that 3-(4'-methoxycarbonyl-1'-butenyl) -6(S)-(3'-oxo-3'-cyclopentyl-trans-1'-propenyl)-7(R)-tetrahydropyranyloxy-(1S,5S)-cis-bicyclo[3.3.0]oct-2-ene (130 mg, 0.29 mmol) was employed as a starting material to obtain 3-(4'-methoxycarbonyl-1'-butenyl)6(S)-(3'(RS)-hydroxy-3'-cyclopentyl-trans-1'-propenyl)7(R)-tetrahydropyranyloxy-(1S,5S)-cis-bicyclo[3.3.0]oct-2-ene (131 mg, Yield: 100%) as a colorless oily product.

IR (neat): 3500, 1742 cm$^{-1}$.

NMR δ(CDCl$_3$): 6.28 (d, J=16Hz, ½H, trans), 6.00 (d, J=11Hz, ⅔H, cis), 5.10–5.80 (m, 4H), 4.70 (m, 1H), 3.70 (s, 3H).

Mass m/z: 444, 342, 298, 220.

(b) The same reaction procedures were carried out as in Example 1-(b) except that 3-(4'-methoxycarbonyl-1'-butenyl)-6(S)-(3'(RS)-hydroxy-3-cyclopentyl-trans-1'-propenyl)-7(R)-tetrahydropyranyloxy-(1S,5S)-cis-bicyclo[3.3.0]oct-2-ene (444 mg, 1 mmol) was employed as a starting material to obtain 3-(4'-methoxycarbonyl-1'-butenyl)-6(S)-(3'(S)-hydroxy-3'-cyclopentyl-trans-1'-propenyl)-7(R)-hydroxy-(1S,5S)-cis-bicyclo[3.3.0]oct-2-ene (Compound B') (198 mg, Yield: 55%) as a colorless oily product.

IR (neat): 3400, 1740 cm$^{-1}$.

NMR δ(CDCl$_3$): 6.22 (d, J=15Hz, ½H, trans), 5.95 (d, J=11Hz, ⅔H, cis), 5.17–5.75 (m, 4H), 3.65 (s, 3H), 3.40–4.00 (m, 2H).

Mass m/z: 360, 342.

$[\alpha]_D^{20} = -30°$ (c=1.16, MeOH).

EXAMPLE 3

Synthesis of Compound C'

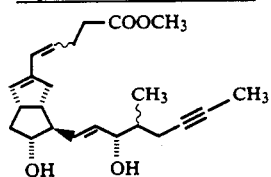

(a) 3-(4'-Methoxycarbonyl-1'-butenyl)-6(S) (3'-oxo-4'(RS)-methyl-trans-1'-octen-6'-ynyl)-7(R)-tetrahydropyranyloxy-(1S,5S) -cis-bicyclo[3.3.0]oct-2-ene (450 mg, 0.99 mmol) was dissolved in methanol (10 ml). To the solution was added an excess amount of sodium borohydride at −25° C. and the mixture was stirred at −25° C. for 1 hour. After the reaction was stopped with addition of acetone, a saturated aqueous ammonium chloride solution was added thereto. Methanol was distilled out and then the residual aqueous layer was extracted with ether. The extract was washed with a saturated aqueous saline solution and thereafter dried with anhydrous magnesium sulfate. The solvent was distilled out and the residue was purified through silica gel column chromatography to obtain 3-(4'-methoxycarbonyl-1'-butenyl)-6(S)-(3'(RS)hydroxy-4'(RS)-methyl-trans-1'-octen-6'-ynyl)-7(R)-tetrahydropyranyloxy-(1S,5S) -cis-bicyclo[3.3.0]oct-2-ene (377 mg, Yield: 84%) as a substantially colorless oily product.

IR (neat): 3500, 1745 cm$^{-1}$.

NMR δ(CDCl$_3$): 6.30, 6.02 (each d, J=16, 12Hz, 1H), 5.20 –5.80 (m, 4H), 4.60 (m, 1H), 3,71 (s, 3H), 1.69 (t, J=2Hz, 3H), 1.00 (m, 3H).

Mass m/z: 372, 354, 85.

(b) 3-(4'-Methoxycarbonyl-1'-butenyl)-6(S)-(3'(RS)-hydroxy-4'(RS)-methyl-trans-1'-octen-6'-ynyl)-7(R)-tetrahydropyranyloxy-(1S,5S) -cis-bicyclo[3.3.0]oct-2-ene (350 mg, 0.77 mmol) was dissolved in THF (0.6 μl). To the solution was added a 65% aqueous acetic acid solution (6 μl) and the mixture was stirred at 50° C. for 2 hours. The reaction mixture was poured into a cooled saturated aqueous sodium hydrogencarbonate solution and extracted with ethyl acetate. The organic layer was washed with a saturated aqueous saline solution and dried with anhydrous magnesium sulfate. The solvent was distilled out and the residue was purified through silica gel column chromatography to obtain 3-(4'-methoxycarbonyl-1'-butenyl)-6(S)-(3'(S)-hydroxy-4'(RS)-methyl-trans-1'-octen-6'-ynyl)-7(R)-hydroxy-(1S,5S)-cis-bicyclo[3.3.0]oct-2-ene (Compound C') (143 mg, Yield: 50%) as a colorless oily product.

IR (neat): 3400, 1740 cm$^{-1}$.

NMR δ(CDCl$_3$): 6.25, 6.00 (each d, J=16, 12 Hz, 1H), 5.00 –5.70 (m, 3H), 3.68 (s, 3H), 1.78 (t, J=2Hz, 3H), 0.98 (m, 3H).

Mass m/z: 372, 354, 336.

$[\alpha]_D^{20} = -16°$ (c=1.86, MeOH).

EXAMPLE 4

Synthesis of Compound D'

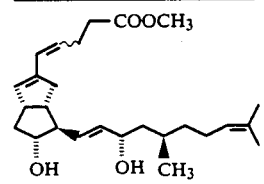

(a) The same reaction procedures were carried out as in Example 3-(a) except that 3-(4'-methoxycarbonyl-1'-butenyl)-6(S)-(3'-oxo-5'(R)-methyl-9'-methyl-trans-1'-decen-8'-enyl)-7(R)-tetrahydropyranyloxy-(1S,5S)-cis-bicyclo[3.3.0]oct-2-ene (490 mg, 0.98 mmol) was employed as a starting material to obtain 3-(4'-methoxycarbonyl-1'-butenyl)-6(S)-(3'(RS)-hydroxy-5'(R)-methyl-9'-methyl trans-1'-decen-8'-enyl)-7(R)-tetrahydropyranyloxy-(1S,5S)-cis-bicyclo[3.3.0]oct-2-ene (492 mg, Yield: 100%) as a substantially colorless oily product.

IR (neat): 3500, 1745 cm$^{-1}$.

NMR δ(CDCl$_3$): 6.26, 6.00 (each d, J=15, 11Hz, 1H), 5.00 –5.62 (m, 5H), 4.68 (m, 1H), 3.69 (s, 3H), 1.68 (s, 3H), 1.58 (s, 3H), 0.90 (d, J=6Hz, 3H).

Mass m/z: 500, 482, 416, 85.

(b) The same reaction procedures were carried out as in Example 3-(1)-(b) except that 3-(4'-methoxycarbonyl-1'-butenyl)-6(S)-(3'(RS)-hydroxy-5'(R)-methyl-9'-methyltrans-1'-decen-8'-enyl)-7(R)-tetrahydropyranyloxy-(1S,5S)-cis-bicyclo-[3.3.0]oct-2-ene (350 mg, 0.70 mmol) was employed as a starting material to obtain 3-(4'-methoxycarbonyl-1'-butenyl)-6(S)-(3' (S)-hydroxy-5'(R)-methyl-9'-methyl-trans-1'-decen-8'- enyl)-7(R)-hydroxy-(1S,5S)-cis-bicyclo[3.3.0]oct-2-ene (Compound D') (126 mg, Yield: 43%) as a substantially colorless oily product.

IR (neat): 3400, 1740 cm$^{-1}$.

NMR δ(CDCl$_3$): 6.25, 6.00 (each d, J=15, 12Hz, 1H), 5.10–5.80 (m, 5H), 3.70 (s, 3H), 1.70 (s, 3H), 1.62 (s, 3H), 0.95 (d, J=6Hz, 3H).

Mass m/z: 416, 398, 380

$[α]_D^{20}$ = −31° (c=2.29, MeOH).

EXAMPLE 5

Synthesis of Compound A

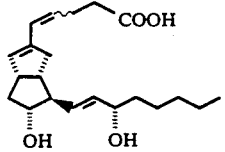

3-(4'-Methoxycarbonyl-1'-butenyl)-6(S)-(3'(S)-hydroxy-1'-trans-octenyl)-7(R)-hydroxy-(1S,5S)-cis-bicyclo[3.3.0]oct-2-ene (15 mg, 0.04 mmol) was dissolved in methanol (0.3 ml). To the solution was added a 10% aqueous sodium hydroxide solution at 0° C. After stirring at 0° C. for 16 hours, the mixture was neutralized with a 10% aqueous hydrochloric acid solution while cooling. Under reduced pressure, methanol was distilled out and, after pH was adjusted to 3–4, the resultant mixture was extracted with ethyl acetate. The extract was dried with anhydrous magnesium sulfate and then the solvent was distilled out to obtain 3-(4'-carboxy-1'-butenyl)-6(S)-(3'(S)-hydroxy-1'-trans-octenyl)-7(R)-hydroxy-(1S,5S)-cis-bicyclo[3.3.0]oct-2-ene (Compound A) (14 mg, Yield: 100%) as a colorless caramel.

IR (neat): 3350, 1720, 1090, 970 cm$^{-1}$.

NMR δ(CDCl$_3$) 6.34 (d, J=16Hz, ½H), 6.00 (d, J=11Hz, ⅜H), 5.65 (m, 3H), 5.45 (m, 1H), 3.10 (m, 1H).

EXAMPLE 6

Synthesis of Compound B

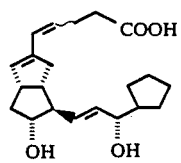

3-(4'-Methoxycarbonyl-1'-butenyl)-6(S)-(3'(S)-hydroxy-3'-cyclopentyl-1'-trans-propenyl)-7(R)-hydroxy-(1S,5S)-cis-bicyclo [3.3.0]oct-2-ene (Compound B') (50 mg, 0.14 mmol) was dissolved in methanol (1.1 ml). To the solution was added a 10% aqueous sodium hydroxide solution (1.1 ml) at 0° C. After stirring at 0° C. for 18 hours, the mixture was neutralized with a 10% aqueous hydrochloric acid solution while cooling. Under reduced pressure, methanol was distilled out and, after pH was adjusted to 3–4, the resultant mixture was extracted with ethyl acetate. The extract was dried with anhydrous magnesium sulfate and then the solvent was distilled out to obtain 3-(4'-carboxy-1'-butenyl)-6(S)-(3'(S)-hydroxy-3'-cyclopentyl-1'-trans-propenyl) -7(R)-hydroxy-(1S,5S)-cis-bicyclo[3.3.0]oct-2-ene (Compound B) (43 mg, Yield: 89%) as a colorless caramel.

IR (neat): 3350, 1715, 1085, 970 cm$^{-1}$.

NMR δ(CDCl$_3$): 6.32 (d, J=16Hz, ½H), 6.04 (d, J=12Hz, ⅜H), 5.64 (m, 3H), 5.44 (m, 1H), 3.10 (m, 1H).

EXAMPLE 7

Synthesis of Compound C

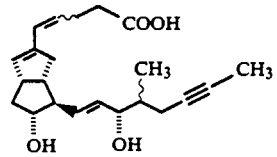

3-(4'-Methoxycarbonyl-1'-butenyl)-6(S)-(3'(S)-hydroxy-4'(RS) -methyl-trans-1'-octen-6'-ynl)-7(R)-hydroxy-(1S,5S)-cis-bicyclo[3.3.0]oct-2-ene (Compound C') (54 mg, 0.145 mmol) was dissolved in methanol (1.16 ml). To the solution was added a 10% aqueous sodium hydroxide solution (1.16 ml) at 0° C. After stirring at 0° C. for 8 hours, the mixture was diluted with ether and then neutralized with a 10% aqueous hydrochloric acid solution while cooling. Under reduced pressure, methanol was distilled out and, after pH was adjusted to 3–4, the resultant mixture was extracted with ethyl acetate. The extract was dried with anhydrous magnesium sulfate and then the solvent was distilled out to obtain 3-(4'-carboxy-1'-butenyl)-6(S)-(3'(S)-hydroxy-4'(RS)-methyl-trans-1'-octen-6'-ynyl)-7(R)-hydroxy-(1S,5S)-cis-bicyclo[3.3.0]oct-2-ene (Compound C) (50 mg, Yield: 96%) as a colorless caramel.

IR (neat): 3350, 2950, 1715 cm$^{-1}$.

NMR δ(CDCl$_3$): 6.32 (d, J=16Hz, ½H), 6.04 (d, J=11Hz, ⅜H), 5.20–5.90 (m, 4H), 1.81 (t, J=2Hz, 3H), 1.00 (m, 3H).

EXAMPLE 8

Synthesis of Compound D

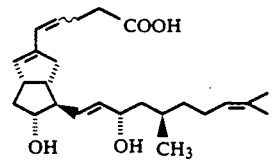

3-(4'-Methoxycarbonyl-1'-butenyl)-6(S)-(3'(S)-hydroxy-5'(R)-methyl-9'-methyl-trans-1'-decen-8'-enyl)-7(R)-hydroxy-(1S,5S)-cis-bicyclo[3.3.0]oct-2-ene (Compound D') (40 mg, 0.086 mmol) was dissolved in methanol (0.69 ml). To the solution was added a 10% aqueous sodium hydroxide solution (0.69 ml) at 0° C. After stirring at 0° C. for 8 hours, the mixture was diluted with ether and then neutralized with a 10% aqueous hydrochloric acid solution while cooling. Under reduced pressure, methanol was distilled out and, after pH was adjusted to 3–4, the resultant mixture was extracted with ethyl acetate. The extract was dried with anhydrous magnesium sulfate and then the solvent was distilled out to obtain 3-(4'-carboxy-1'-butenyl)-6(S)-(3'(S)-hydroxy-5'(R)-methyl-9'-methyl-trans-1'-decen-8'-enyl)-7(R)-hydroxy(1S,5S)-cis-bicyclo[3.3.0]oct-2-ene (Compound D) (37 mg, Yield: 95%).

IR (neat): 3350, 2950, 1715 cm$^{-1}$.

NMR δ(CDCl₃): 6.30 (d, J=16Hz, ½H), 6.02 (d, J=11Hz, ½H), 5.28-5.75 (m, 4H), 5.12 (t, J=7Hz, 1H), 1.61 (s, 3H), 1.68 (s, 3H), 0.93 (d, J=6Hz, 3H).

EXAMPLE 9

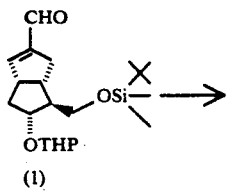
(1)

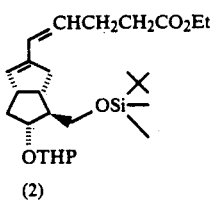
(2)

Under argon gas atmosphere, 216 mg (9.0 mmol) of sodium hydride was suspended in 10 ml of dimethyl sulfoxide and stirred at 50° C. for 30 minutes to prepare a solution, followed by cooling to 20° C. To this solution was added dropwise a solution of 4.11 g (9.0 mmol) of (3-ethoxycarbonyl)propyltriphenylphosphonium bromide in dimethyl sulfoxide (7 ml). After stirring for 30 minutes, a solution of 1.14 g (3.0 mmol) of 3-formyl-6(R)-tertbutyldimethylsiloxy-7(R)-tetrahydropyranyloxy-bicyclo[3.3.0]oct-2-ene (1) in dimethyl sulfoxide (10 ml) was added, followed by stirring at room temperature for one hour. The reaction mixture was poured into water, extracted with ether, dried over MgSO₄, and concentrated under reduced pressure to obtain a crude product. This was purified by column chromatography (ethyl ether/hexane =3/2) to obtain 1.37 g of 3-(4'-ethoxycarbonyl-1'-butenyl)-6(R)-tert-butyldimethylsiloxy-7(R)-tetrahydropyranyloxy-bicyclo[3.3.0]oct-2-ene (Compound 2). Yield: 97%.

IR (neat): 1735, 1135, 1020, 835 cm⁻¹.

NMR δ(CDCl₃): 5.90 (d, J=11Hz, 0.9H), 5.4-5.6 (m, 1H), 4.9-5.4 (m, 1H), 4.4-4.7 (m, 1H), 4.05 (q, J=7Hz, 2H), 1.20 (t, J=7Hz, 3H), 0.89 (s, 9H), 0.05 (s, 6H).

EXAMPLE 10

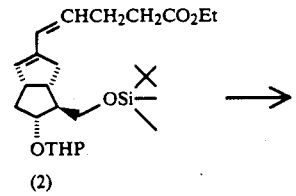
(2)

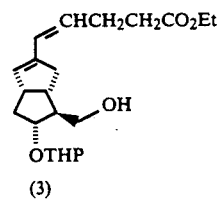
(3)

To a solution of 1.30 g (2.7 mmol) of the Compound (2) dissolved in 30 ml of tetrahydrofuran was added under room temperature 4 ml (40 mmol) of a tetrahydrofuran solution of tetrabutylammonium fluoride (1M). After stirring at room temperature for 5 hours and at 0° C. overnight, the reaction mixture was poured into an aqueous NaHCO₃ solution, followed by extreffect with ethyl ether. The extract was dried over MgSO₄, concentrated under reduced pressure, and the crude product obtained was purified by column chromatography (ethyl ether/hexan=2/1) to obtain 936 mg of 3-(4'-ethoxycarbonyl-1'-butenyl)-6(R)-hydroxy-7(R)-tetrapyranyloxybicyclo[3.3.0]oct-2-ene (Compound 3). Yield: 95%.

IR (neat): 3450, 1730, 1370, 1350, 810 cm⁻¹.

NMR δ(CDCl₃) 5.83 (d, J=11Hz, 0.9H), 5.5 - 5.7 (m, 1H), 5.0-5.5 (m, 1H), 4.11 (q, J=7Hz, 2H), 1.28 (t, J=7Hz, 3H).

EXAMPLE 11

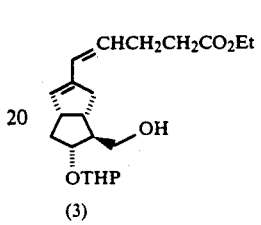
(3)

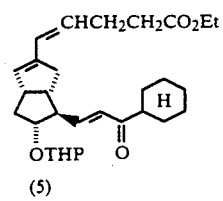
(4)

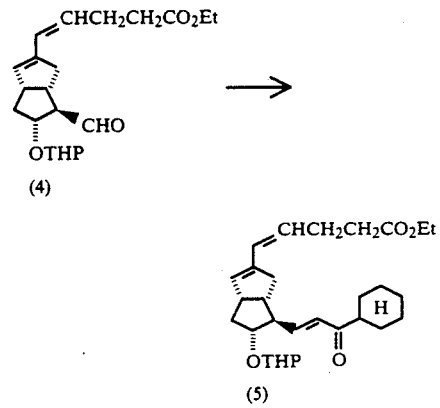
(5)

Under argon gas atmosphere, 60 mg (0.16 mmol) of the alcohol derivative (3) was dissolved in 0.8 ml of triethylamine and 0.5 ml of dimethyl sulfoxide and to the resultant solution was added dropwise a solution of 534 mg of SO₃ - pyridine complex in dimethyl sulfoxide (2 ml). After stirring for 30 minutes, the reaction mixture was poured into ice-cold water, extracted with ethyl ether, dried over MgSO₄ and concentrate to obtain a crude aldehyde (4).

Under argon gas atmosphere 13 mg (60%, 0.32 mmol) of sodium hydride was suspended in tetrahydrofuran and a solution of 82 mg (0.35 mmol) of dimethyl(2-cyclohexyl-2-oxoethyl)phosphonate was added under room temperature. After stirring for 30 minutes, a solution of the above crude aldehyde (4) in tetrahydrofuran (2 ml) was added, followed further by stirring for one hour. The reaction mixture was poured into ice-cold water, extracted with ethyl ether, dried over MgSO₄ and the solvent was evaporated to give a crude product. This was purified by thin layer chromatography (hexane/ethyl ether=1/1) to obtain 66 mg of an α,β-unsaturated carbonyl compound (Compound 5). Yield: 86%.

IR (neat): 1735, 1680, 1665, 1625 cm⁻¹.

NMR δ(CDCL₃): 6.0-7.1 (m, 2H), 5.81 (d, J=11Hz, 0.9H), 5.5-5.7 (m, 1H), 5.0-5.5 (m, 1H), 4.4-4.7 (m, 1H), 4.08 (q, J=7Hz, 2H), 1.25 (t, J=7Hz, 3H).

EXAMPLE 12

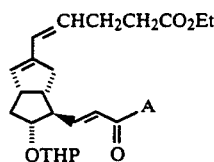

According to the same procedure as in Example 11, the following compounds were synthesized. In Table 1, yields and spectra data are shown.

TABLE 1

| A | Yield (%) | Spectrum data |
|---|---|---|
| CH$_3$—CH(CH$_3$)—C≡C—CH$_3$ | 35 | IR (neat): 1730, 1688, 1668, 1625 cm$^{-1}$. NMR δ (CDCl$_3$): 5.9–7.1 (m, 2H), 5.88 (d, J=11Hz, 0.9H), 5.0–5.7 (m, 2H), 4.4–4.7 (m, 1H), 4.08 (q, J=7Hz, 2H), 0.9–1.4 (m, 9H). |
| CH$_3$CH$_2$—C(CH$_3$)=CH—CH$_3$ | 73 | IR (neat): 1730, 1675, 1615 cm$^{-1}$. NMR δ (CDCl$_3$): 5.9–6.8 (m, 2H), 5.88 (d, J=11Hz, 0.9H), 5.0–5.7 (m, 2H), 4.4–4.7 (m, 1H), 4.05 (q, J=7Hz, 2H), 0.9–1.4 (m, 9H). |
| (CH$_3$)$_2$CH—(CH$_2$)$_3$—CH$_3$ | 100 | IR (neat): 1735, 1690, 1683, 1622 cm$^{-1}$. NMR δ (CDCl$_3$): 6.0–7.1 (m, 2H), 5.82 (d, J=11Hz, 0.9H), 5.5–5.7 (m, 1H), 5.0–5.5 (m, 1H), 4.4–4.7 (m, 1H), 4.04 (q, J=7Hz, 2H), 0.8–1.5 (m, 9H). |
| —CH$_2$—CH$_2$—Ph | 79 | IR (neat): 1730, 1670, 1620 cm$^{-1}$. NMR δ (CDCl$_3$): 7.20 (s, 5H), 6.0–6.9 (m, 2H), 5.95 (d, J=11Hz, 0.9H), 5.0–5.7 (m, 2H), 4.4–4.7 (m, 1H), 4.10 (q, J=7Hz, 2H), 1.25 (t, J=7Hz, 3H). |
| (CH$_3$)$_3$C—CH$_2$—CH$_3$ | 100 | IR (neat): 1730, 1690, 1685, 1625 cm$^{-1}$. NMR δ (CDCl$_3$): 5.9–6.9 (m, 2H), 5.96 (d, J=11Hz, 0.9H), 5.0–5.7 (m, 2H), 4.4–4.7 (m, 1H), 4.1 (q, J=7Hz, 2H), 1.3 (s, 6H). |
| (CH$_3$)$_2$CH—(CH$_2$)$_2$—CH$_3$ | 73 | IR (neat): 1735, 1690, 1665, 1625 cm$^{-1}$. NMR δ (CDCl$_3$): 5.95–6.8 (m, 2H), 5.85 (d, J=11Hz, 0.9H), 5.0–5.7 (m, 2H), 4.4–4.7 (m, 1H), 4.05 (q, J=7Hz, 2H). |
| (CH$_3$)$_2$CH—cyclohexyl | 86 | IR (neat): 1735, 1692, 1665, 1623 cm$^{-1}$. NMR δ (CDCl$_3$): 6.0–7.0 (m, 2H), 5.88 (d, J=11Hz, 0.9H), 5.0–5.7 (m, 2H), 4.4–4.7 (m, 1H), 4.05 (q, J=7Hz, 2H). |
| CH$_3$—CH(CH$_3$)—CH$_2$—CH$_3$ | 88 | IR (neat): 2950, 1730, 1688, 1664, 1624 cm$^{-1}$. Mass m/z: 388, 370, 327, 257, 211, 169, 85, 43. |

EXAMPLE 13

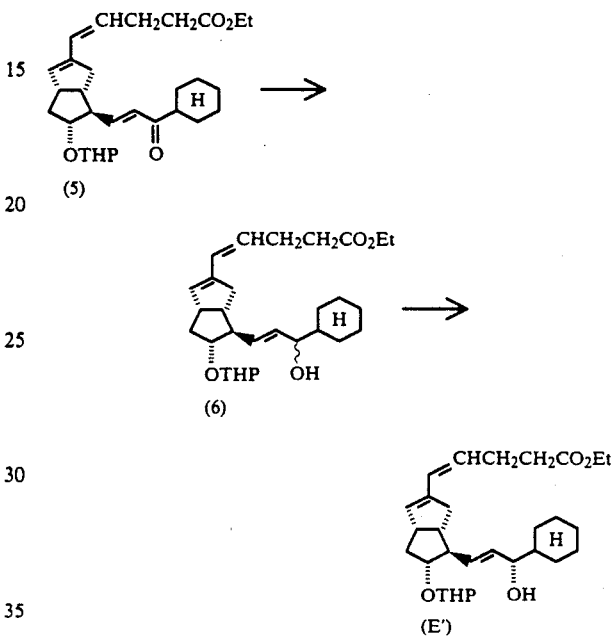

To a solution of 60 mg (0.13 mmol) of the α,β-unsaturated ketone (Compound 5) dissolved in 5 ml of methanol, a solution of 6.0 mg of sodium borohydride in methanol (1 ml) was added at −78° C. After one hour, the reaction mixture was elevated in temperature to −20° C., at which the mixture was further stirred for one hour. The reaction was stopped by addition of acetone, and the reaction mixture was poured into aqueous saturated ammonium chloride, extracted with ethyl ether and concentrated under reduced pressure to give a crude alcohol (6). The crude alcohol was dissolved in aqueous 65% acetic acid and the solution was stirred under heating at 50° C. for 2 hours. After cooling of the reaction mixture, it was poured into an aqueous NaHCO$_3$ solution, extracted with ethyl acetate, dried over MgSO$_4$, followed by evaporation of the solvent, to give a crude product. This was purified by thin layer chromatography to obtain 29 mg of a 15α-diol derivative (E') as high polar component.

IR (neat): 3450, 1730 cm$^{-1}$.

NMR δ(CDCl$_3$): 5.90 (d, J=11Hz, 0.9H), 4.9–5.8 (m, 4H), 4 5–4.8 (m, 1H), 4.07 (q, J=7Hz, 2H), 1.25 (t, J=7Hz, 3H).

EXAMPLE 14

According to the same procedure as in Example 13, the following compounds were synthesized. In Table 2, yields and spectra data are shown.

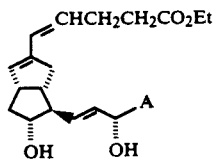

TABLE 2

| Compound | A | Yield (%) | Spectrum data |
|---|---|---|---|
| F' | CH3-CH(CH3)-C≡C-CH3 | 54 | IR (neat): 3360, 1730 cm$^{-1}$. Mass m/z: 400, 382, 271, 234, 117, 81. |
| G' | CH3CH2-C(CH3)=C-CH3 | 23 | IR (neat): 3350, 1735 cm$^{-1}$. NMR δ (CDCl$_3$): 5.91 (d, J=11Hz, 0.9H), 5.0–5.7 (m, 4H), 4.07 (q, J=7Hz, 2H), 1.23 (t, J=7Hz, 3H). |
| H' | CH3-CH(CH3)-CH2CH2CH2-CH3 | 48 | IR (neat): 3380, 1735 cm$^{-1}$. NMR δ (CDCl$_3$): 5.89 (d, J=11Hz, 0.9H), 5.0–5.6 (m, 4H), 4.05 (q, J=7Hz, 2H), 0.7–1.0 (m, 9H). |
| I' | CH2CH2-phenyl | 33 | IR (neat): 3360, 1730 cm$^{-1}$. NMR δ (CDCl$_3$): 7.16 (s, 5H), 5.92 (d, J=11Hz, 0.9H), 5.0–5.7 (m, 4H), 4.04 (q, J=7Hz, 2H), 1.20 (t, J=7Hz, 3H). |
| J' | C(CH3)2-CH2CH2-CH3 | 52 | IR (neat): 3400, 1730 cm$^{-1}$. Mass m/z: 386, 368, 311, 287, 192, 143, 91. |
| K' | CH3CH2-CH(CH3)-CH2CH2-CH3 | 46 | IR (neat): 3350, 1735 cm$^{-1}$. Mass m/z: 386, 368, 283, 192, 131, 91. |
| L' | CH(CH3)-cyclohexyl | 39 | IR (neat): 3370, 1735 cm$^{-1}$. Mass m/z: 398, 380, 315, 297, 192, 81. |
| M' | CH2-CH(CH3)-CH2CH2-CH3 | 47 | IR (neat): 3350, 2960, 2925, 2870, 1735, 1155, 970 cm$^{-1}$. NMR δ (CDCl$_3$): 6.27 (d, J=15Hz, 0.1H), 5.99 (d, J=11Hz, 0.9H), 5.3–5.7 (m, 4H), 4.16 (m, 1H), 4.13 (q, J=7.3Hz, 2H), 3.8 (m, 1H), 3.08 (m, 1H). Mass m/z: 372, 354, 328, 234. |

EXAMPLE 15

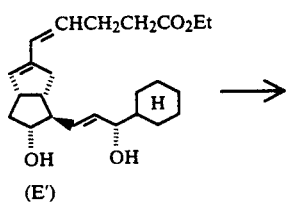

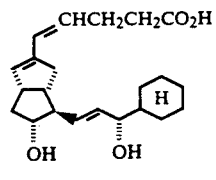

To a solution of 29 mg (0.075 mmol) of the 15α-diol derivative (Compound E') dissolved in 2 ml of ethanol, 1 ml of an aqueous 5% sodium hydroxide solution was added under room temperature, followed by stirring for one hour. After completion of the reaction, the reaction mixture was carefully neutralized with a 5N hydrochloric acid finally to pH 4 to 3. This was extracted with ethyl acetate, dried over MgSO$_4$ and the solvent evaporated to give a crude product. This was purified through a neutral silica gel capillary column to obtain 23 mg of a carboxylic acid (E). Yield: 85%.

IR (neat): 3350, 1700 cm$^{-1}$.

NMR δ(CDCl$_3$): 6.29 (d, J=15Hz, 0.1H), 6.10 (d, J=11Hz, 0.9H), 5.4–5.7 (m, 3H), 5.3–5.4 (m, 1H), 3.7–3.9 (m, 2H), 3.0–3.2 (m, 1H). Mass m/z: 342, 324.

EXAMPLE 16

According to the same procedure as in Example 15, the following compounds were synthesized. In Table 3, yields and spectra data are shown.

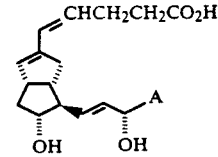

TABLE 3

| Compound | A | Yield (%) | Spectrum data |
|---|---|---|---|
| F | CH3-CH(CH3)-C≡C-CH3 | 52 | NMR δ (CDCl$_3$): 6.28 (d, J=15Hz, 0.1H), 6.01 (d, J=11Hz, 0.9H), 5.2–5.7 (m, 4H), 3.7–4.2 (m, 2H), 3.1 (m, 1H), 0.9–3.0 (m, 23H). Mass m/z: 354, 336, 259, 177, 91, 81. |
| G | CH3CH2-C(CH3)=C-CH3 | 59 | IR (neat): 3320, 1700 cm$^{-1}$. NMR δ (DMSO-d$_6$): 6.23 (d, J=15Hz, 0.1H), 5.97 (d, J=11Hz, 0.9H), 5.2–5.7 (m, 4H), 3.9–4.2 (m, 1H), 0.9–1.2 (m, 6H). |
| H | CH3-CH(CH3)-CH2CH2CH2-CH3 | 96 | IR (neat): 3350, 1705 cm$^{-1}$. NMR δ (CDCl$_3$): 6.28 (d, J=15Hz, 0.1H), 6.01 (d, J=11Hz, 0.9H), 5.4–5.7 (m, 3H), 3.9–4.1 (m, 1H), 3.7–0.9 (m, 1H), 0.8–1.0 (m, 6H). Mass m/z: 358, 340. |

TABLE 3-continued

| Compound | A | Yield (%) | Spectrum data |
|---|---|---|---|
| I | ~~⟨phenyl⟩ (CH2CH2-phenyl) | 89 | IR (neat): 3340, 1700 cm$^{-1}$. NMR δ (CDCl$_3$): 7.1–7.5 (m, 5H), 6.29 (d, J=15Hz, 0.1H), 6.01 (d, J=11Hz, 0.9H), 5.5–5.8 (m, 3H), 5.3–5.5 (m, 1H), 4.1–4.2 (m, 1H), 3.7–3.9 (m, 1H). Mass m/z: 364, 346. |
| J | (CH$_3$)$_2$C(CH$_3$)-CH$_2$-C(CH$_3$)$_2$-... | 52 | NMR δ (CDCl$_3$): 6.28 (d, J=15Hz, 0.1H), 6.01 (d, J=11Hz, 0.9H), 5.3–5.8 (m, 4H), 3.83 (m, 2H), 3.10 (m, 1H), 1.1–2.8 (m, 20H), 0.89 (s, 3H), 0.85 (s, 3H). Mass m/z: 358, 340, 314, 259, 206, 164, 95, 57. |
| K | CH(CH$_3$)CH$_2$CH$_2$CH$_3$ branched | 63 | NMR δ (CDCl$_3$): 6.28 (d, J=15Hz, 0.1H), 6.01 (d, J=11Hz, 0.9H), 5.3–5.7 (m, 4H), 4.19 (m, 1H), 3.78 (m, 1H), 1.0–3.2 (m, 25H), 0.89–0.93 (two d, 3H). Mass m/z: 358, 340, 314, 259, 206, 164, 117, 57. |
| L | cyclohexyl-CH(CH$_3$)- | 91 | NMR δ (CDCl$_3$): 6.28 (d, J=15Hz, 0.1H), 6.01 (d, J=11Hz, 0.9H), 5.2–5.7 (m, 4H), 4.05 (m, 1H), 3.80 (m, 1H), 0.8–3.5 (m, 25H), 0.76 (d, J=7.3 Hz, 3H). Mass m/z: 370, 352, 326, 259, 206, 164, 81, 55. |
| M | CH(CH$_3$)CH$_2$CH$_3$ iso | 73 | IR (neat): 3350, 2950, 2860, 1700 cm$^{-1}$. NMR δ (CDCl$_3$): 6.28 (d, J=15Hz, 0.1H), 6.00 (d, J=11Hz, 0.9H), 5.2–5.7 (m, 4H), 4.20 (m, 1H), 3.80 (dd, J=16, 9.5Hz, 1H), 3.06 (m, 1H). Mass m/z: 344, 326, 300, 177. |

(Preparation of pharmaceutical)

EXAMPLE 17

5 mg of 3-(4'-methoxycarbonyl-1'-butenyl)-6(S)-(3'-(S)-hydroxy-trans-1'-octenyl)-7(R)-hydroxy-(1S,5S)-cis-bicyclo[3.3.0]oct-2-ene (Compound A') dissolved in 5 ml of ethanol, 0.2 g of carboxymethyl cellulose calcium, 20 mg of silicon dioxide, 0.2 g of magnesium stearate and 5 g of mannitol were mixed and dried according to a conventional method. The mixture was made up to 10 g with addition of mannitol and then mixed sufficiently until it became uniform. The resultant mixture was directly punched by use of a mortar and a pounder according to a conventional manner to obtain 100 tablets containing 50 μg of the active substance in one tablet.

EXAMPLE 18

70 mg of β-cyclodextrin inclusion compound (content of Compound B': 5 mg) included therein 3-(4'-methoxycarbonyl-1'-butenyl)-6(S)-(3'(S)-hydroxy-3'-cyclopentyltrans-1'-propenyl)-7(R)-hydroxy-(1S,5S)-cis-bicyclo[3.3.0]oct-2-ene (Compound B'), 0.2 g of carboxymethyl cellulose calcium, 20 mg of silicon dioxide, 0.2 g of magnesium stearate and dried mannitol were mixed such that the mixture was made up to 10 g and then mixed sufficiently until it became uniform. The resultant mixture was directly punched by use of a mortar and a pounder according to a conventional manner to obtain 100 tablets containing 50 μg of the active substance in one tablet.

EXAMPLE 19

The same procedures were carried out as in Example 1 except that 10 mg of 3-(4'-methoxycarbonyl-1'-butenyl)6(S)-(3'(S)-hydroxy-4'(RS)-methyl-trans-1'-octen-6'ynyl)-7(R)-hydroxy-(1S,5S)-cis-bicyclo[3.3.0]oct-2-ene (Compound C') was employed as a starting material to obtain 100 tablets containing 100 μg of the active substance in one tablet.

EXAMPLE 20

70 mg of β-cyclodextrin inclusion compound (content of Compound D': 5 mg) included therein 3-(4'-methoxycarbonyl-1'-butenyl)-6(S)-(3'(S)-hydroxy-5'(R)-methyl-9'-methyl-trans-1'-decen-8'-enyl)-7 (R)-hydroxy-(1S,5S)-cis-bicyclo[3.3.0]oct-2-ene (Compound D'), 0.23 g of magnesium stearate and lactose were mixed such that the mixture was made up to 2.3 g and then mixed sufficiently until it became uniform. The resultant mixture was charged into a gelatin capsule No. 3 according to a conventional method to obtain 100 capsules wherein 50 μg of an active substance was contained in each capsule.

EXAMPLE 21

14 mg of β-cyclodextrin inclusion compound (content of Compound C': 1 mg) included therein 3-(4'-methoxycarbonyl-1'-butenyl)-6(S)-(3'(S)-hydroxy-4'(RS)-methyl-trans-1'-octen-6'-ynyl)-7(R)-hydroxy-(1S,5S)-cis-bicyclo[3.3.0]oct-2-ene (Compound C'), was dissolved in 100 ml of a distilled water. The resultant solution was sterilized according to a conventional manner and aliquots each of 1 ml were injected into ampoules of 5 ml capacity to obtain 100 injection preparations containing 10 μg of the active substance in one injection.

EXAMPLE 22

A solution of 5 mg of 3-(4'-carboxy-1'-butenyl)-6(S)-(3'(S)-hydroxy-3'-cyclohexyl-trans-1'-propenyl)-7(R)-hydroxy-(1S,5S)-cis-bicyclo [3.3.0]oct-2-ene (Compound E) dissolved in 5 ml of ethanol, 0.2 g of carboxymethyl cellulose calcium, 20 mg of silicon dioxide, 0.2 g of magnesium stearate and 5 g of mannitol were mixed in a conventional manner and dried. Then, mannitol was added to a total weight of 10 g, followed by thorough mixing until homogeneous, and the resultant mixture was tabletted directly by means of a mortar and a pestle to obtain 100 tablets containing 50 μg of the active substance in one tablet.

EXAMPLE 23

For Compound E', Compound F, Compound F,, Compound G, Compound G', Compound H, Compound H', Compound I, Compound I', Compound J, Compound J', Compound K, Compound K', Compound L, Compound L', Compound M and Compound M', according to the same procedure as in Example 22, 100 tablets containing 50 μg of the active substance in one tablet were obtained.

EXAMPLE 24

A blend of 70 mg [content of Compound E': 5 mg] of α-cyclodextrin inclusion compound of 3-(4'-ethoxycarbonyl-1'-butenyl)-6(S)-(3'(S)-hydroxy-3'-cyclohexyl-trans-1'-propenyl)-7(R)-hyroxy-(1S,5S)-cis-bicyclo[3.3.0]oct-2-ene (Compound E'), 0.2 g of carboxymethyl cellulose calcium, 20 mg of silicon dioxide, 0.2 g of magnesium stearate and the balance of mannitol added to make up 10 g was thoroughly mixed until homogeneous, and tabletted directly in a conventional manner to obtain 100 tablets containing 50 ug of the active substance in one tablet.

EXAMPLE 25

A blend of 70 mg [content of Compound F: 5 mg] of β-cyclodextrin inclusion compound of 3-(4'-carboxy-1'-butenyl)-6(S)-(3'(S)-hydroxy-4'(RS)-methyl-trans-1'-nonen-6'-ynyl)-7(R)-hyroxy-(1S,5S)-cis-bicyclo[3.3.0]oct2-ene (Compound F), 0.23 g of magnesium stearate and the balance of lactose added to make up 23 g, was thoroughly mixed until homogeneous and filled in No. 3 gelatin capsules in a conventional manner to obtain 100 capsules containing 50 μg of the active substance in on capsule.

EXAMPLE 26

A solution of 14 mg [content of Compound G': 1 mg] of β-cyclodextrin inclusion compound of 3'-(4'-ethoxycarbonyl-1'-butenyl)-6(S)-(3'-(S)-hydroxy-5'(RS)-methyltrans-1'-nonen-6'-ynyl)-7(R)-hydroxy-(1S,5S)-cis-bicyclo[3.3.0]oct-2-ene (Compound G') dissolved in 100 ml of distilled water was sterilized in a conventional manner, and aliquots each of 1 ml were injected into ampoules of 5 ml capacity to obtain 100 injection preparations containing 10 μg of the active substance in one ampoule.

EXPERIMENT 1

Vasodilative effect (Method)

Female and male adult dogs were anesthetized by intraveneous administeration of 30 mg/kg of sodium pentobarbital and fixed on their back positions. The right femoral artery was perfused at constant flow with the dog's own blood by means of a peristaltic pump (Harvard Co.). The perfusion pressure was measured with an electromanometer and systemic blood pressure was measured in the other femoral artery with a pressure transducer. As an anticoagulant, 500 U/kg of heparin sodium was intravenously administered.

The compound of the present invention was dissolved in 10 % ethanol - 90% physiological salt solution and administered into arterial blood through a thick rubber tube provided in the perfusion circuit. The vasodilative effect of the compound of the present invention is expressed by the change ratio of perfusion pressure after administration into the artery. The results are shown in the following Table.

TABLE 4

| Compound No. | Administration route | Dose (μg/kg) | Perfusion pressure change (%) |
| --- | --- | --- | --- |
| Compound A | intraarterial | 100 | −18 |

TABLE 4-continued

| Compound No. | Administration route | Dose (μg/kg) | Perfusion pressure change (%) |
| --- | --- | --- | --- |
| Compound B | intraarterial | 100 | −12 |
| Compound C | intraarterial | 100 | −23 |
| Compound D | intraarterial | 100 | −28 |
| OP-41483 | intraarterial | 100 | −16 |

EXPERIMENT 2

Hypotensive effect (Method)

Male wistar strain rats (weighing 240-290 g) were anesthetized by intraperitoneal administration of 50 mg/kg of sodium pentobarbital, and blood pressures were measured. The compound of the present invention was administered intravenously as a solution dissolved in 10% ethanol - 90% physiological salt solution. The hypotensive effect is expressed by the percent change of average blood pressure after intravenous administration (relative to that before administration). The results are shown in the following Table 5.

TABLE 5

| Hypotensive effect in anesthetited rats | | | |
| --- | --- | --- | --- |
| Compound No. | Administration route | Dose (μg/kg) | Percent change (%) |
| Compound A | intravenous | 3 | −43 |
| Compound B | intravenous | 1 | −34 |
| Compound C | intravenous | 0.3 | −40 |
| Compound D | intravenous | 3 | −38 |
| OP-41483 | intravenous | 10 | −39 |

EXPERIMENT 3

Platelet aggregation inhibiting effect (Method)

Bloods were sampled from healthy volunteers (22–34 years old) with no administration of drug for 2 weeks or more early in the morning when they were hungry. By use of an injector filled with 5 ml of 3.8% sodium citrate solution, 50 ml of blood was sampled, immediately stirred by turning upside down and centrifuged at 200xg for 15 minutes. The supernatant was separated as the PRP (platelet rich plasma) and the residue further subjected to centrigugation at 2000xg for 15 minutes, followed by recovery of the supernatant as PPP (poor platelet plasma) which was provided for use in the experiment.

PRP (250 μl) was placed in a cuvette, 5 μl of an 1% ethanol solution of the compound of the present invention or an 1% ethanol solution was added, and incubation was carried out at 37° C. for one minute. Then, an aggregation inducing agent (ADP) was added and the process of aggregation was recorded by Aggregometer (Sienco Co.).

As the concentration of ADP, the minimum concentration of ADP (2–10 μM) to give the maximum aggregation for respective platelets were employed. The inhibition percentage of platelet aggregation was calculated by the following formula:

Inhibition percentage = (A − B)/A × 100

A: Maximum aggregation ratio during addition of solvent (1% ethanol solution)

B: Maximum aggregation ratio during addition of the compound of the present invention.

The platelet aggregation inhibiting effects of the compounds of the present invention are shown in terms of $IC_{50}$ values in Table 6.

TABLE 6

| Human platelet aggregation inhibiting effect (in vitro) | |
|---|---|
| Compound No. | Platelet aggregation inhibiting ratio ($IC_{50}$) |
| Compound A | $1.4 \times 10^{-8}$ M |
| Compound B | $7 \times 10^{-9}$ M |
| Compound C | $8 \times 10^{-10}$ M |
| Compound D | $2 \times 10^{-8}$ M |
| Compound E | $5 \times 10^{-9}$ M |
| Compound F | $4 \times 10^{-9}$ M |
| Compound G | $6 \times 10^{-10}$ M |
| Compound H | $8 \times 10^{-9}$ M |
| Compound I | $8 \times 10^{-8}$ M |
| Compound J | $2 \times 10^{-7}$ M |
| Compound K | $2 \times 10^{-9}$ M |
| Compound L | $3 \times 10^{-7}$ M |
| Compound M | $4 \times 10^{-9}$ M |
| OP-41483 | $9 \times 10^{-9}$ M |

EXPERIMENT 4

Antiulcer effect (1)

(Method)

Male SD-strain rats (weighing 220-255 g) were fasted for 20 hours (water was given ad libitum) and, after further abstinence from food and water for 4 hours, the compound of the present invention was administered orally, followed further by oral administration of 1 ml of 0.6 N hydrochloric acid 30 minutes later. One hour after administration of hydrochloric acid, the stomach was enucleated under chloroform anesthesia. The fluid in the stomach was discharged and 7.5 ml of a 1% formalin solution was injected into the stomach to fix the gastric mucosa. Then, the stomach was dissected along the greater curvature and the length of the gastric mucosa damage was measured under a steroscopic microscope. The compound of the present invention was dissolved in 5% ethanol - 95% physiological salt solution and administered at a dose of 25 μg/kg in a volume of 5 ml/kg.

The antiulcer effect of the compound of the present invention was calculated by the following formula:

$$\text{Percent inhibition of gastric mucosa damage by HCl} = \frac{lo - l}{lo} \times 100 \, (\%)$$

l: length of gastric mucosa damage in the group to which the compound of the present invention is administered;

lo: length of gastric mucosa damage in the group of non-administration of drug.

The results are shown in the following Table 7.

TABLE 4

| Compound No. | Antiulcer effect | | |
|---|---|---|---|
| | Administration route | Dose (μg/kg) | Inhibition of gastric mocosa damage (%) |
| Compound C | Oral | 25 | 95.5 |
| Compound D | Oral | 25 | 91.5 |
| PGE₂ | Oral | 25 | 61.1 |
| OP-41483 | Oral | 25 | −28.3 |

TABLE 4-continued

| Compound No. | Antiulcer effect | | |
|---|---|---|---|
| | Administration route | Dose (μg/kg) | Inhibition of gastric mocosa damage (%) |
| | | | (worsened) |

EXPERIMENT 5

Antiulcer effect (2)

(Method)

Male wistar strain rats (weighing 250-280 g) were fasted for 18 hours subjected to peritoneotomy under ether anesthesia for ligature of pylorus, and after 4 hours under abstinence from food and water, gastric juice was sampled. The gastric juice was centrifuged at 3000 rpm for 10 minutes, and then the amount, pH and acidity of the gastric juice were measured. The acidity was measured by titration by means of an automatic titrating device (Toa Denpa Kogyo) with a 0.1N NaOH to pH 7.0 and calculating according to the following formula:

$$\frac{\text{Titration amount (0.1N NaOH) required for 1 ml sample}}{\text{Titration amount (0.1N NaOH) required for 1 ml 0.1N HCl}} \times 0.1 \, (N) \times 1000 \, (mEq/l)$$

The gastric juice secretion inhibition percentage was calculated according to the following formula:

$$\text{Inhibition percentage} = \frac{A - B}{A} \times 100$$

A: Amount of gastric acid excreted in Control group
B: Amount of gasatric acid excreted in Drug group
The drugs to be tested were administered subcutaneously immediately after pylorus ligature. The results are shown in Table 8.

TABLE 8

| Compound No. | Rat gastric acid inhibiting effect | | |
|---|---|---|---|
| | Dose (μg/kg) | Amount of gastric acid secreted (mEq/l) | Inhibition (%) |
| Solvent | — | 73.6 | — |
| Compound E | 100 | 28.7 | 61.0 |
| Compound F | 100 | 13.4 | 81.8 |
| Compound G | 100 | 25.3 | 65.6 |
| Compound H | 100 | 7.4 | 89.9 |
| Compound I | 100 | 19.5 | 73.5 |
| Compound J | 100 | 60.3 | 18.1 |
| Compound K | 100 | 21.7 | 70.5 |
| Compound L | 100 | 46.5 | 36.8 |
| Compound M | 100 | 19.5 | 73.5 |

We claim:
1. A prostaglandin $I_2$ analogue for circulation amelioration having the following formula:

$$\text{=CHCH}_2\text{CH}_2\text{COOR}$$

(structure with $CH_3$ groups, OH substituents, and terminal $CH_3$)

wherein R represents a hydrogen atom, a methyl group or an ethyl group.

2. The prostaglandin $I_2$ analogue according to claim 1, wherein R is a hydrogen atom.

3. The prostaglandin $I_2$ analogue according to claim 1, wherein R is a methyl group.

4. The prostaglandin $I_2$ analogue according to claim 1, wherein R is an ethyl group.

* * * * *